(12) United States Patent
Corbett et al.

(10) Patent No.: US 10,512,537 B2
(45) Date of Patent: Dec. 24, 2019

(54) FLOW OPTIMIZED POLYMERIC HEART VALVE

(75) Inventors: Scott C. Corbett, Beverly, MA (US); Mike Finnegan, North Reading, MA (US); Stephen Vaughan, Medford, MA (US); Jeffery Juretich, Herriman, UT (US)

(73) Assignee: ABIOMED, INC., Danvers, MA (US)

( * ) Notice: Subject to any disclaimer, the term of this patent is extended or adjusted under 35 U.S.C. 154(b) by 1266 days.

(21) Appl. No.: 12/761,891

(22) Filed: Apr. 16, 2010

(65) Prior Publication Data

US 2011/0257738 A1 Oct. 20, 2011

(51) Int. Cl.
A61F 2/24 (2006.01)

(52) U.S. Cl.
CPC .......... *A61F 2/2412* (2013.01); *A61F 2/2415* (2013.01); *A61F 2/2409* (2013.01); *A61F 2250/0036* (2013.01)

(58) Field of Classification Search
CPC .................................... A61F 2/06; A61F 2/24
USPC ............................................... 623/2.18, 2.19
See application file for complete search history.

(56) References Cited

U.S. PATENT DOCUMENTS

| | | | |
|---|---|---|---|
| 5,037,434 A | 8/1991 | Lane | |
| 5,116,564 A | 5/1992 | Jansen | |
| 5,258,023 A | 11/1993 | Reger | |
| 6,117,169 A | 9/2000 | Moe | |
| 6,165,215 A * | 12/2000 | Rottenberg et al. | ......... 623/2.12 |
| 2003/0114924 A1 | 6/2003 | Moe | |
| 2004/0024452 A1 | 2/2004 | Kruse et al. | |
| 2004/0088046 A1 * | 5/2004 | Speziali | ....................... 623/2.19 |
| 2009/0222082 A1 | 9/2009 | Lock et al. | |

FOREIGN PATENT DOCUMENTS

| | | |
|---|---|---|
| JP | H02168961 | 6/1990 |
| JP | 2002-537946 A | 11/2002 |
| JP | 2003504152 A | 2/2003 |
| JP | 2010-527745 A | 8/2010 |
| WO | WO-93/18721 | 9/1993 |
| WO | WO1998032400 | 7/1998 |
| WO | WO-98/51239 | 11/1998 |

(Continued)

OTHER PUBLICATIONS

AU Examination Report for Application No. 2011239561 dated Jan. 20, 2014.

(Continued)

*Primary Examiner* — Matthew W Schall
(74) *Attorney, Agent, or Firm* — White & Case LLP

(57) ABSTRACT

A polymeric heart valve is disclosed which includes a valve body having a central axis and including a conduit extending along the central axis from an inflow end to an outflow end; and at least three flexible leaflets extending from the body into the conduit, each of the leaflets defining an attachment curve with the body. Respective pairs of leaflets each define a commissure located proximal the body. The at least three leaflets define a partially open position at rest, a fully open position deflecting away from the central axis during forward blood flow along a direction from the inflow end to the outflow end, and a closed position deflecting toward the central axis during reverse blood flow along a direction from the outflow end to the inflow end.

19 Claims, 14 Drawing Sheets

(56) References Cited

FOREIGN PATENT DOCUMENTS

| | | |
|---|---|---|
| WO | WO2003063740 | 8/2003 |
| WO | WO2007016251 | 2/2007 |
| WO | WO2007130537 | 11/2007 |

OTHER PUBLICATIONS

International Search Report for PCT/US2011/032559 dated Jul. 9, 2011.
International Search Report for PCT/US2011/032560, dated Aug. 16, 2011.

* cited by examiner

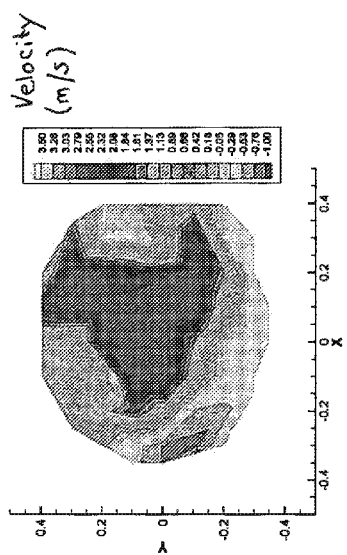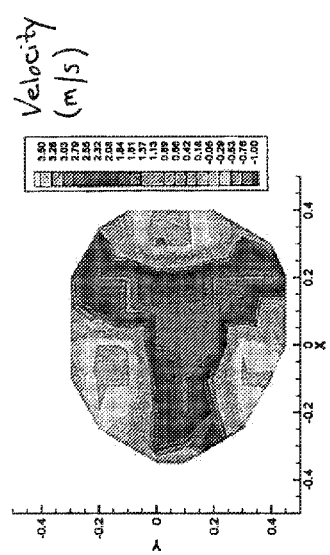

FLOW OPTIMIZED POLYMERIC HEART VALVE

RELATED APPLICATION

The present application is related to U.S. application Ser. No. 12/761,931 entitled PERCUTANEOUS VALVE DEPLOYMENT filed Apr. 16, 2010, the entire contents of which are incorporated herein by reference.

BACKGROUND

Prosthetic heart valves are used to replace damaged or diseased heart valves. Prosthetic heart valves for human patients have been available since the 1950s. Today, there are three general types of prosthetic heart valves, including mechanical valves, tissue valves, and polymer valves. A heart valve prosthesis is implanted into an annular opening in a patient's heart following surgical removal of a diseased or damaged natural valve. The valve can be secured in the annulus of the opening through the use of sutures or pins that penetrate the host tissue and an outside edge of the valve. Alternatively, the valve can be secured in the annulus by suturing the host tissue to a sewing ring. Heart valves function essentially as one-way check valves for blood flow through the beating heart.

The term "mechanical valve" refers to mono or bi-leaflet heart valves having a valve orifice fabricated at least in part of a rigid, biologically compatible material such as pyrolytic carbon, and comprising essentially no biological components. The term "bioprosthetic valve" refers to a bi-leaflet or tri-leaflet heart valve having at least some biological components such as tissue or tissue components. The biological components of tissue valves are obtained from a donor animal (typically bovine or porcine), and the valve may comprise either biological materials alone or biological materials with man-made supports or stents. The term "polymeric valve" refers to a tri-leaflet or bi-leaflet heart valve having at least some elastomeric polymer components, including at least elastomeric polymer valve leaflets.

A tri-leaflet heart valve prosthesis typically includes an annular valve body and three flexible leaflets attached thereto. The valve body includes an annular base and three leaflet support posts, called a "stent," located at the circumference of the annulus. A sewing ring annularly coupled to the periphery of the valve body provides a place for sutures to be applied when the valve is implanted. The leaflets are attached to the three shaped posts along an attachment curve, and they also have a free, unattached edge end remote from the attachment curve. The place where two adjacent leaflets come together at one of the support posts is called the commissure, and the generally curved area on the leaflet between the free edge and the attachment curve is known as the belly of the leaflet. The free edges of the three leaflets come together at a "triple point" generally on the axis of the valve.

When blood flows in the forward direction, the energy of the blood flow deflects the three leaflets away from the center of the annulus and allows blood to flow through. When blood flows in the reverse direction, the three leaflets engage each other in a coaptive region, occlude the valve body annulus and prevent the flow of blood.

SUMMARY

Polymeric heart valves are required to have high durability, hemocompatibility and hemodynamic performance. Leaflet thickness is key to achieving these requirements. Prior art leaflets are made sufficiently thick in order to produce durable valves resulting in excessively high forward flow pressure loss and incomplete leaflet opening. The present embodiments provide the use of thicker leaflets without sacrificing forward flow pressure loss performance or incomplete leaflet opening.

In one aspect, an exemplary polymeric heart valve is disclosed, including: a valve body having a central axis and including a conduit extending along the central axis from an inflow end to an outflow end; and at least three flexible leaflets extending from the body into the conduit, each of the leaflets defining an attachment curve with the body. Respective pairs of leaflets each define a commissure located proximal the body. The at least three leaflets define a partially open position at rest, a fully open position deflecting away from the central axis during forward blood flow along a direction from the inflow end to the outflow end, and a closed position deflecting toward the central axis during reverse blood flow along a direction from the outflow end to the inflow end.

Some embodiments further include, for each leaflet, a respective sinus lobe in the conduit extending along the valve body and located distal the respective leaflet from the inflow end.

In some embodiments, the energy required to move the leaflets from the partially open position at rest to the open position during forward blood flow is less than the energy required to open the leaflets of an equivalent valve formed in a closed position at rest.

In some embodiments, the at least three leaflets open symmetrically in response to forward blood flow.

In some embodiments, in the open position, the blood flow velocity through each commissure is substantially the same as that blood flow velocity through the other commissures.

In some embodiments, each leaflet includes a pair of free edges coming to a tip near the central axis of the body.

In some embodiments, each leaflet is characterized by at least a four point thickness profile, where: the first point in the profile is substantially located at the tip of the leaflet; the second point and the third point in the leaflet are substantially located at respective commissures; and the fourth is substantially located proximal the body substantially midway along the attachment curve between the second and third points.

In some embodiments, the first point has a thickness ranging between about 0.25 mm and about 0.5 mm. In some embodiments, the second point and the fourth point, each has a thickness ranging between about 0.3 mm and about 0.7 mm. In some embodiments, the third point has a thickness ranging between about 0.2 mm and about 0.4 mm.

In some embodiments, the first point has a thickness ranging between about 0.1 mm and about 0.25 mm. In some embodiments, the second point and the fourth point, each has a thickness ranging between about 0.15 mm and about 0.3 mm. In some embodiments, the third point has a thickness ranging between about 0.1 mm and about 0.2 mm.

In some embodiments, the first point has a thickness about equal to or less than two thirds of the thickness of the second and fourth points.

In some embodiments, the first point has a thickness about equal to or less than one half of the thickness of the second and fourth points.

In some embodiments, the third point has a thickness about equal to or less than two thirds of the thickness of the second and fourth points.

In some embodiments, the at rest opening of adjacent leaflets closest to their respective commissure ranges between 0.1 mm and 0.6.

In some embodiments, the at rest opening of adjacent leaflets closest to their respective commissure is 0.25 mm.

In some embodiments, the body, sinus lobes, and leaflets are made from a biocompatible polymer.

In some embodiments, the biocompatible polymer is selected from a group consisting of silicone and/or polyurethane.

In some embodiments, the body, sinus lobes, and leaflets are integrally constructed.

Some embodiments further include at least one sewing ring coupled to the body above or below the sinuses and leaflets to provide a place for sutures to be applied when the valve is implanted.

In another aspect, an exemplary method of making a polymeric heart valve is disclosed including: forming a polymeric valve including: a valve body having a central axis and including a conduit extending along the central axis from an inflow end to an outflow end; and at least three flexible leaflets extending from the body into the conduit, each of the leaflets defining an attachment curve with the body; where respective pairs of leaflets each define a commissure located proximal the body, and where the leaflets are in a substantially closed at rest position. The method further includes inserting a tapered form into the conduit to maintain the at least three leaflets in a partially open position; heating the polymeric valve to fix the rest position of the at least three leaflets in the partially open position; and after the heating, removing the form.

In some embodiments, each leaflet includes a pair of free edges coming to a tip near the central axis of the body; and where inserting a tapering form into the annular body to maintain the at least three leaflets in a partially open position includes using the tapered form to deflect the tip of each leaflet away from the central axis.

In some embodiments, the tapered form includes at least three pins, and where inserting the tapered form into the annular body includes positioning each of the at least three pins in a respective commissure.

In some embodiments, the tapered form includes a conical portion having a slope of at least about 25 degrees.

In some embodiments, heating the polymeric valve to fix the rest position of the at least three leaflets in the partially open position includes heating the valve to a temperature of about 125° C. for at least about 2 hours.

In some embodiments, after the form is removed, the at least three leaflets define a partially open position at rest, a fully open position deflecting away from the central axis during forward blood flow, and a closed position deflecting toward the central axis during reverse blood flow.

Some embodiments further include trimming each of the at least three leaflets to provide a desired thickness profile.

In some embodiments, trimming each of the at least three leaflets includes using a hot wire to remove at least a portion of polymeric material from the leaflet.

In some embodiments, the desired thickness profile of each leaflet includes at least a four point thickness profile, where: the first point in the profile is substantially located at the tip of the leaflet; the second point and the third point in the leaflet are substantially located at respective commissures; and the fourth is substantially located proximal the body substantially midway along the attachment curve between the second and third points. In various embodiments the thickness profiles may be as described above.

In some embodiments, the body, sinus lobes, and leaflets are made from a biocompatible polymer.

In some embodiments, the biocompatible polymer is selected from a group consisting of silicone and/or polyurethane.

In some embodiments, the body and leaflets are integrally constructed.

In some embodiments, at least one sewing ring is coupled to the body above or below the sinuses and leaflets to provide a place for sutures to be applied when the valve is implanted.

In another aspect, an exemplary polymeric heart valve is disclosed which prepared by a process including the steps of: forming a polymeric valve including: a valve body having a central axis and including a conduit extending along the central axis from an inflow end to an outflow end; and at least three flexible leaflets extending from the body into the conduit, each of the leaflets defining an attachment curve with the body; where respective pairs of leaflets each define a commissure located proximal the body, and where the leaflets are in a substantially closed at rest position. The process further includes the steps of: inserting a tapered form into the conduit to maintain the at least three leaflets in a partially open position; heating the polymeric valve to fix the rest position of the at least three leaflets in the partially open position; and after the heating, removing the form.

Various embodiments may include any of the features described above, alone or in any suitable combination.

The present embodiments provide at least the following advantages over prior art prosthetic heart valves. First, setting the leaflets in an open position ensures low forward flow pressure loss. Second, the leaflet geometry ensures symmetric opening to prevent low fluid velocities in the commissures between the leaflets and in the sinus lobes distal to each leaflet.

BRIEF DESCRIPTION OF THE DRAWINGS

FIG. 3A is a mean velocity plot for a valve cast in the closed rest position at peak systole;

FIG. 3B is a mean velocity plot for a valve having a partially open rest position at peak systole;

DETAILED DESCRIPTION

Generally, the present technology relates to polymeric heart valves that increase valve reliability and reduce forward flow pressure loss. The polymeric heart valve includes a body and at least three flexible leaflets, with pairs of adjacent leaflets defining commissures located therebetween. The valve leaflets are formed in a partially open position at rest to ensure low forward flow pressure loss and symmetric opening.

Figure 1A:
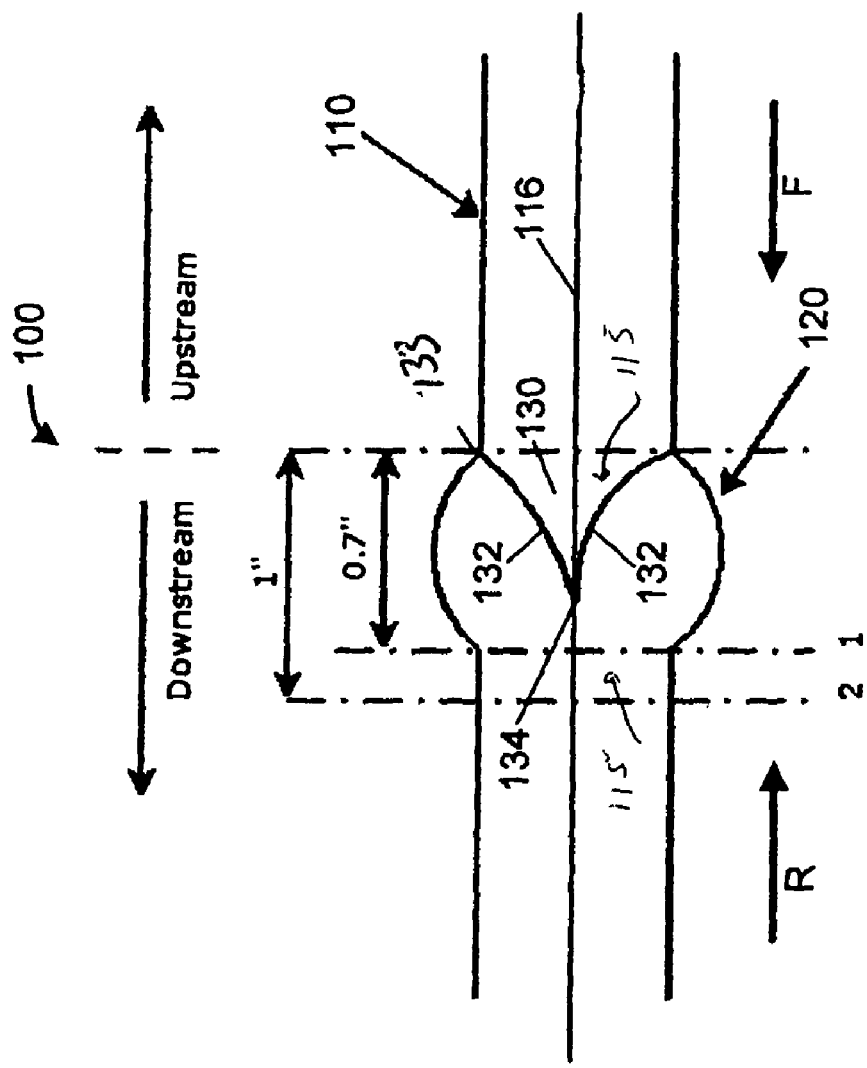
FIG. 1A is a cross-sectional view of the polymeric heart valve.
Figure 1B:
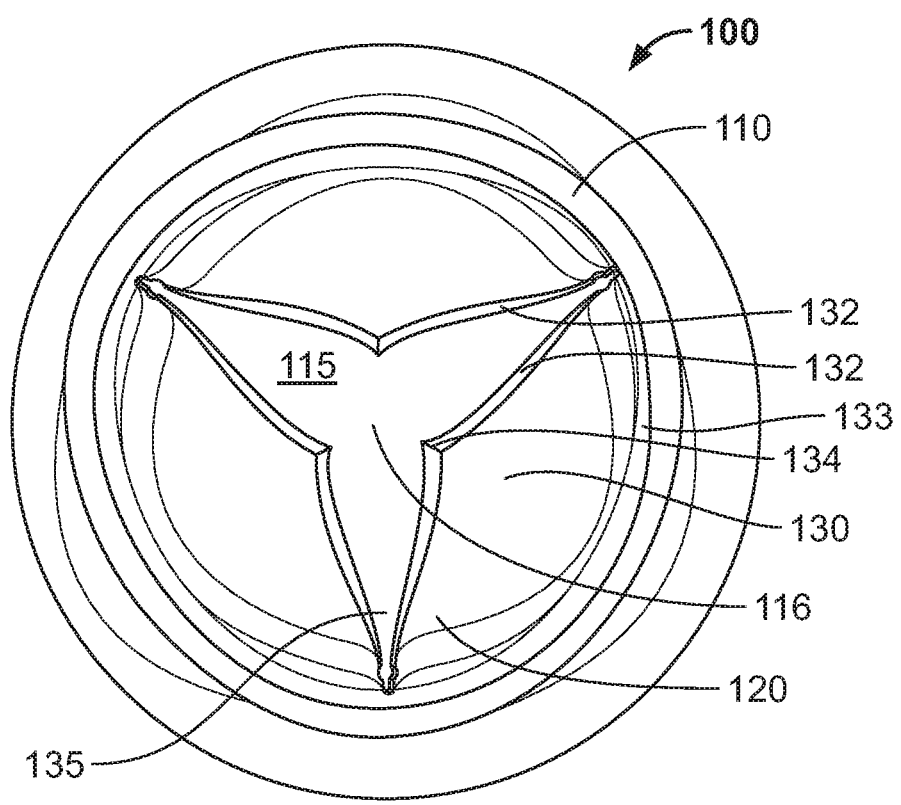
FIG. 1B is a top down view of a polymeric heart valve of FIG. 1A in the at rest position.

FIGS. 1A and 1B show one embodiment of a polymeric heart valve 100. The heart valve includes an annular, generally cylindrical elastomeric valve body 110 having a conduit 115 extending along and about a central axis 116 from an inflow end to an outflow end. Valve 100 includes at least three flexible leaflets 130 each having a pair of free edges 132 coming to a tip 134 near the central axis 116 of the body 110. Each of the leaflets attach to the valve body 110 at an attached edge 133, defining an attachment curve. Each pair of leaflets defines a commissure 135 therebetween. In some embodiments, valve body 110 includes at least three sinus lobes 120 extending in an axial direction about the body 110, each located distal a respective leaflet. In one embodiment, the body 110, the sinus lobes 120, and the leaflets 130 can be made from a biocompatible polymer.

As shown, the leaflets 130 are cast in a partially open position at rest (i.e. in the absence of forward or reverse fluid pressure against the valve). For example, the open area of the valve in the at rest position (e.g., the open cross sectional area presented to fluid flow through the valve) may be a suitable fraction of the open area of the valve in the absence of the leaflets 130. In some embodiments the open area in the partially open at rest positions may be greater than 5%, 10%, 25% or more of the open area, e.g., in the range of 5-10%, 10-20%, 10-30%, or any other suitable range.

Figure 7:
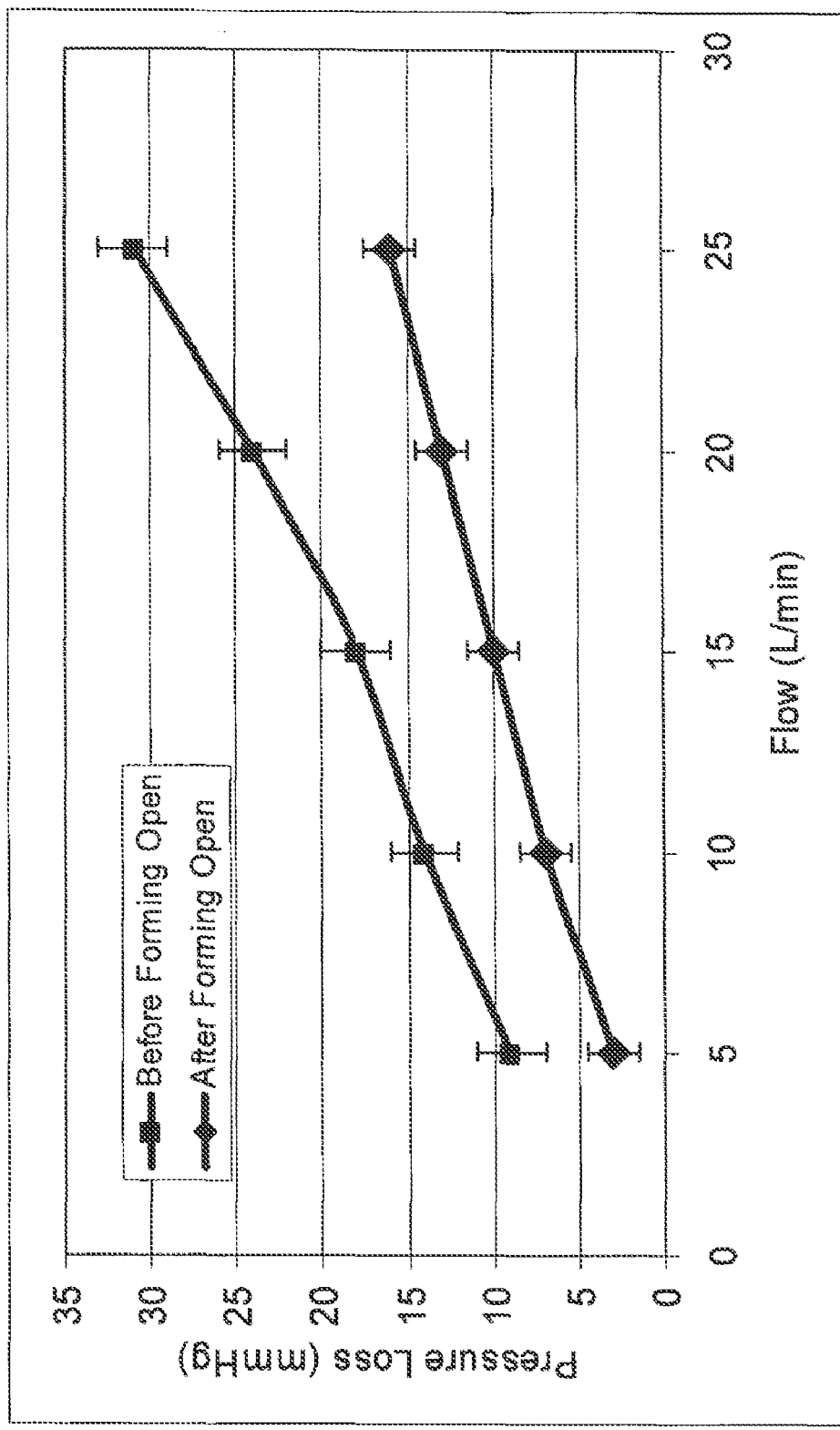
FIG. 7 is a plot of pressure loss versus flow for a valve formed in a partially open position and an equivalent valve formed in a closed position.

This configuration reduces the energy required to open the leaflets during forward blood flow relative to that required to open an equivalent valve which is formed in a closed position at rest. The relative ease of opening of valve 100 when formed in the partially open rest position results in a decrease in forward flow pressure loss. For example, FIG. 7 illustrates the improved forward flow for an exemplary valve formed in the partially open at rest position, relative to the equivalent valve formed in the closed at rest position.

Furthermore, the partially open rest position leaflet 130 geometry helps ensure a symmetric opening of the leaflets in response to forward flow. For example, by providing the leaflets 130 in the partially open rest configuration, the valve can avoid unwanted adhesion of free edges of one or more pairs of adjacent leaflets 130 to one another. This prevents low fluid velocities in the commissure 135 between the leaflets 130 and in the sinus lobes 120 distal to each leaflet 130. As discussed in detail below, avoiding low fluid flow and/or asymmetric flow patterns can lead to a reduction or even elimination of deleterious effects, e.g., thrombosis.

Figure 1C:
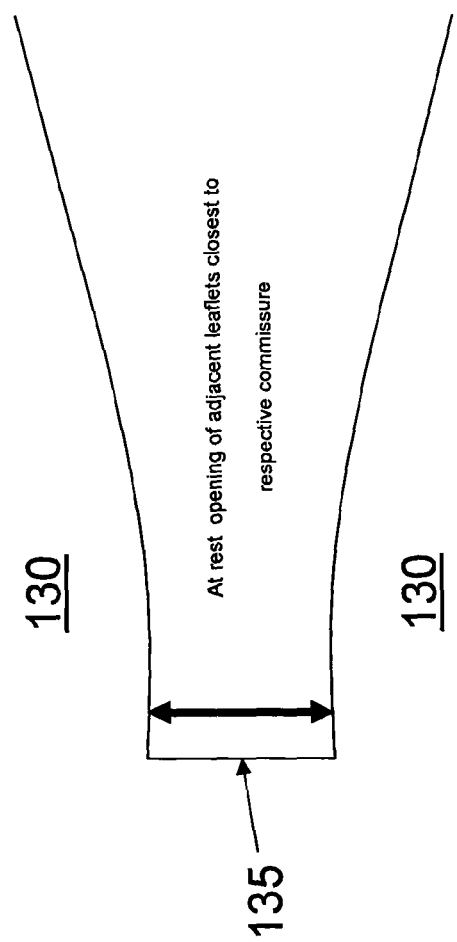
FIG. 1C is an illustration of the commissure region of the polymeric heart valve of FIG. 1A in the at rest position.

The at rest opening of adjacent leaflets 130 closest to their respective commissure ranges between 0.1 mm and 0.6 mm, as shown in detail in FIG. 1C. In one embodiment, the at rest opening is 0.25 mm. As described in greater detail below, to set the leaflets 130 in a partially open position at rest, a form, e.g. a tapered form, is placed in the valve body 110 forcing the leaflets 130 into the partially open position after which the valve 100 is annealed giving the leaflets 130 a partially open "memory" position which persists after removal of the form. Note that although a tapered conical form is used in the examples presented below, any appropriately shaped form (e.g. a cylindrical form) may be used to hold the leaflets 130 in the partially open position.

In operation, when blood flows in the forward direction, i.e. in the direction of the arrow F shown in FIG. 1A (from the inflow end towards the outflow end of the valve body 110), the pressure of the blood flow causes the leaflets 130 to deflect away from a central axis 116 of the valve body 110. In this "open" position, the leaflets 130 define a large flow orifice (not shown) allowing the blood to flow freely in the forward direction. With the leaflets 130 in the open position, the valve 100 presents little resistance to fluid flow. When blood flows in the reverse direction, i.e. in the direction of the arrow R shown in FIG. 1A (from the outflow end towards the inflow end of the valve body 110), the pressure of the blood flow fills the sinus lobes 120 causing the leaflets 130 to deflect toward the central axis 116. In this "closed" position, each leaflet 130 engages the adjacent leaflets 130 along the free edges 132, causing the valve 100 to seal against reverse flow.

Figure 2:
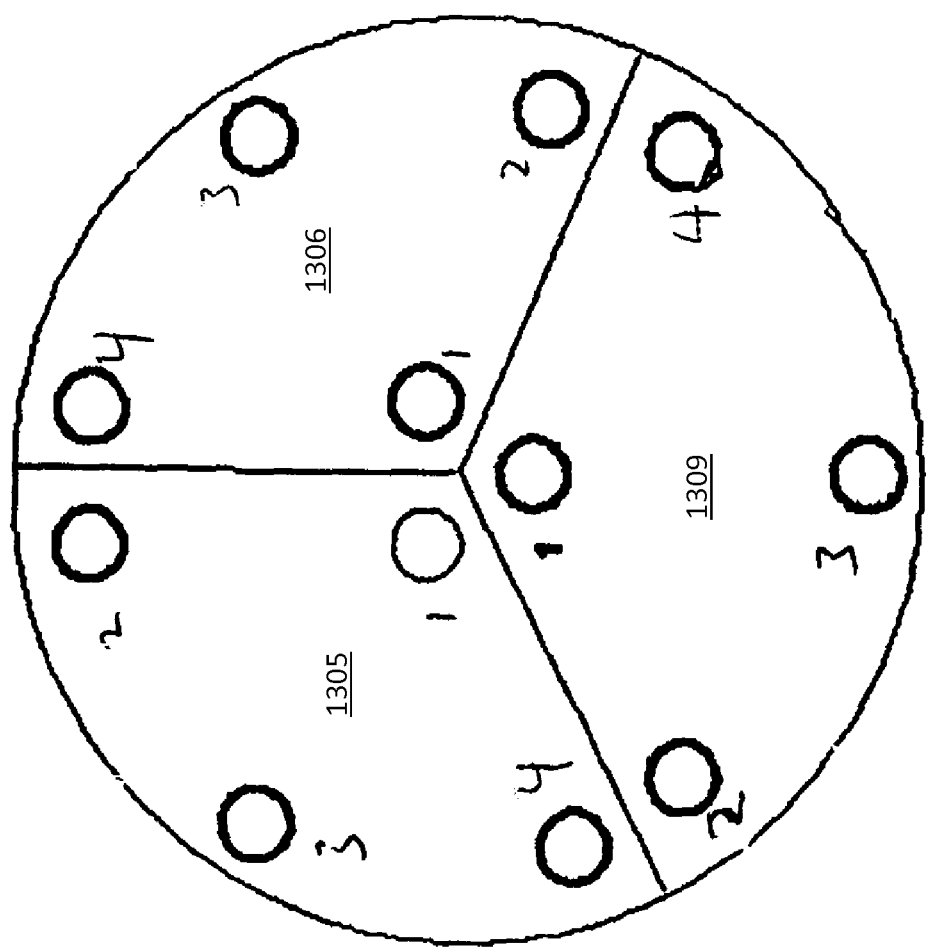
FIG. 2 is a leaflet thickness profile of the polymeric heart valve.

FIG. 2 is a leaflet thickness profile of the leaflets 130 of the polymeric heart valve 100 of FIGS. 1A and 1B. As shown, each leaflet 130a, 130b, and 130c is characterized by a four point thickness profile. As shown, point 1 is located near (e.g., within about 1 mm of) the tip of the leaflet 130a. Points 2 and 4 are located near (e.g., within about 1 mm of) the attached edge 133 of the leaflet 130a, close to (e.g., within about 1 mm of) the commissures 135 formed with adjacent leaflets 130b and 130c, respectively. Point 3 is located near (e.g., within about 1 mm of) attached edge 133, between points 2 and 4.

In some applications, the leaflet profile is critical for the integrity of the leaflets 130 during operation of the valve. The correct thickness profile provides increased valve 100 reliability and reduces forward flow pressure losses. In some embodiments, the leaflet 130a will taper as it extends away from the body 110 to the tip 134. Accordingly, the thickness at point 1 may be less than the thickness at points 2 and 4. For example, in some embodiments, the thickness at point 1 is less than about two thirds of the thickness at points 2 and 3, less than about two thirds of the thickness at points 2 and 4, or even less, e.g. in the range from about one half to about two thirds of the thickness at points 2 and 4.

In some embodiments, the leaflet 130a is thicker near its free edges 132 than its central region. Accordingly, the thickness at point 3 may be less than the thickness at points 2 and 4. For example, in some embodiments, the thickness at point 3 is about two thirds of the thickness at points 2 and 4, or even less, e.g. in the range from about one half to about two thirds of the thickness at points 2 and 4. In some embodiments, the thickness of leaflet 130a varies continuously between points 1, 2, 3, and 4 to form a "scoop" shaped profile.

Exemplary thickness ranges for each of the thickness profile points is shown in Table 1. Thickness ranges as shown in Table 1 are suitable, e.g., for a valve used in a vascular assist device.

TABLE 1

| | Thickness Profile (mm) | | | |
|---|---|---|---|---|
| Point | 1 | 2 | 3 | 4 |
| Leaflet 1 | 0.25-0.51 | 0.30-0.66 | 0.20-0.41 | 0.30-0.66 |
| Leaflet 2 | 0.25-0.51 | 0.30-0.66 | 0.20-0.41 | 0.30-0.66 |
| Leaflet 3 | 0.25-0.51 | 0.30-0.66 | 0.20-0.41 | 0.30-0.66 |

TABLE 2

| | Thickness Profile (mm) | | | |
|---|---|---|---|---|
| Positions | 1 | 2 | 3 | 4 |
| Leaflet 1 | 0.10-0.25 | 0.15-0.30 | 0.075-0.20 | 0.15-0.30 |
| Leaflet 2 | 0.10-0.25 | 0.15-0.30 | 0.075-0.20 | 0.15-0.30 |
| Leaflet 3 | 0.10-0.25 | 0.15-0.30 | 0.075-0.20 | 0.15-0.30 |

Of course, for various applications, other suitable thickness profiles may be used. In some applications in which valve 100 is included in a replacement heart valve implant, the leaflets 130 may have a thickness profile as shown in Table 2 above. Note that this example maintains the thickness profile rations of the example from Table 1, but is overall thinner. In various embodiments, the ratios may be maintained but other thicknesses provided. In further embodiments, other suitable ratios may be used.

FIGS. 3A and 3B show mean flow velocity plots for an exemplary valve formed with a closed rest position (FIG. 3A) according to the prior art and an equivalent exemplary valve 100 formed in the partially open rest position (FIG. 3B) according to the embodiments described herein. A mock circulatory loop was used to evaluate the flow fields during the entire cardiac cycle the two polymeric trileaflet heart valves in the aortic position. Each valve was manufactured within a conduit (as shown in FIG. 1A) and attached to the outlet port of the 50 cc ventricle in the mock loop. The fluid used in the loop was a Newtonian blood analog consisting of 12% glycerin, 28% water and 60% sodium iodide solution by volume to match as closely to the refractive index of the conduit as possible. The fluid had a density of 1.91 g/cm$^3$, a kinematic viscosity of 3.77 centistokes and an index of refraction of 1.51.

Each valve was tested at a heart rate of 90 beats/minute, a flow rate of 4.5 liters/minute, and a systolic duration of 35%. The flow rate in the loop was measured using an ultrasonic flow probe (Transonic Systems, Ithaca, N.Y.) located approximately eight inches downstream of the valve. Near physiologic atrial and aortic pressures were maintained for both valves during data collection. A one-dimensional laser Doppler velocimetry system was used to measure the axial velocities along the flow at 60 points in the flow field.

With respect to FIG. 1A, two planes of data were collected at 0.7 inches from the base of the leaflets 130 and 1 inch from the base of the leaflets 130. For each spatial location (0.1 inches apart), 10,000 velocity measurements were acquired over a sufficient number of cardiac cycles. During post processing, the data was divided into 10 ms time bins over the entire cardiac cycle (667 ms). FIGS. 3A and 3B display mean velocities at peak systole for the closed and partially open polymeric valves, respectively.

FIG. 3A (closed at rest valve) clearly shows asymmetric flow fields with retrograde flow up to 1 m/s encompassing a significant amount of area behind one of the leaflets (lower left hand corner) suggesting this leaflet does not open completely. There is a minor amount of retrograde flow behind the other two leaflets with the highest retrograde mean velocity of −0.98 m/s. These retrograde flow fields indicate areas that have the potential for thrombus formation. Peak mean velocities near 2.79 m/s are present during peak systole in the central orifice and persist for approximately 30 ms (not shown) of the cardiac cycle. The maximum velocity measured was 3.56 m/s with a maximum retrograde velocity of −1.63 m/s. Flow near the commissures is significant between only two leaflets (upper right hand corner), while lower velocities are seen between the other leaflets. Lower velocities between the leaflets may lead to thrombus formation.

FIG. 3B (partiality open at rest valve) displays a better overall flow pattern (e.g., more symmetric) at the same flow rate with significant flow between the commissures. There are similar peak velocities (2.99 m/s) but over a greater area and retrograde flows (−0.84 m/s) behind each leaflet compared to the closed valve, displaying better washout in these regions. The largest forward velocity measured was 3.56 m/s with the maximum retrograde velocity slightly higher at −1.67 m/s. Unlike the closed valve, all three leaflets for the open formed valve behave more consistently as evidenced by the uniform flow field. This flow field develops and remains for approximately 30 ms. Thus, the data suggests that the open formed valve has equivalent, or potentially improved hemocompatibility when compared to the closed formed valve. The open formed valve has excellent washing between all of the leaflets in the commissure area. For example, as indicated in FIG. 3B, flow rates of about 2.0 m/s or greater are found in the regions directly adjacent the commissure. The retrograde flow is symmetrically distributed behind all leaflets, which encourages proper vortex formation in the sinus lobes (e.g., substantially conformal to the sinuses of Valsalva) located distal to each leaflet.

Figure 4:
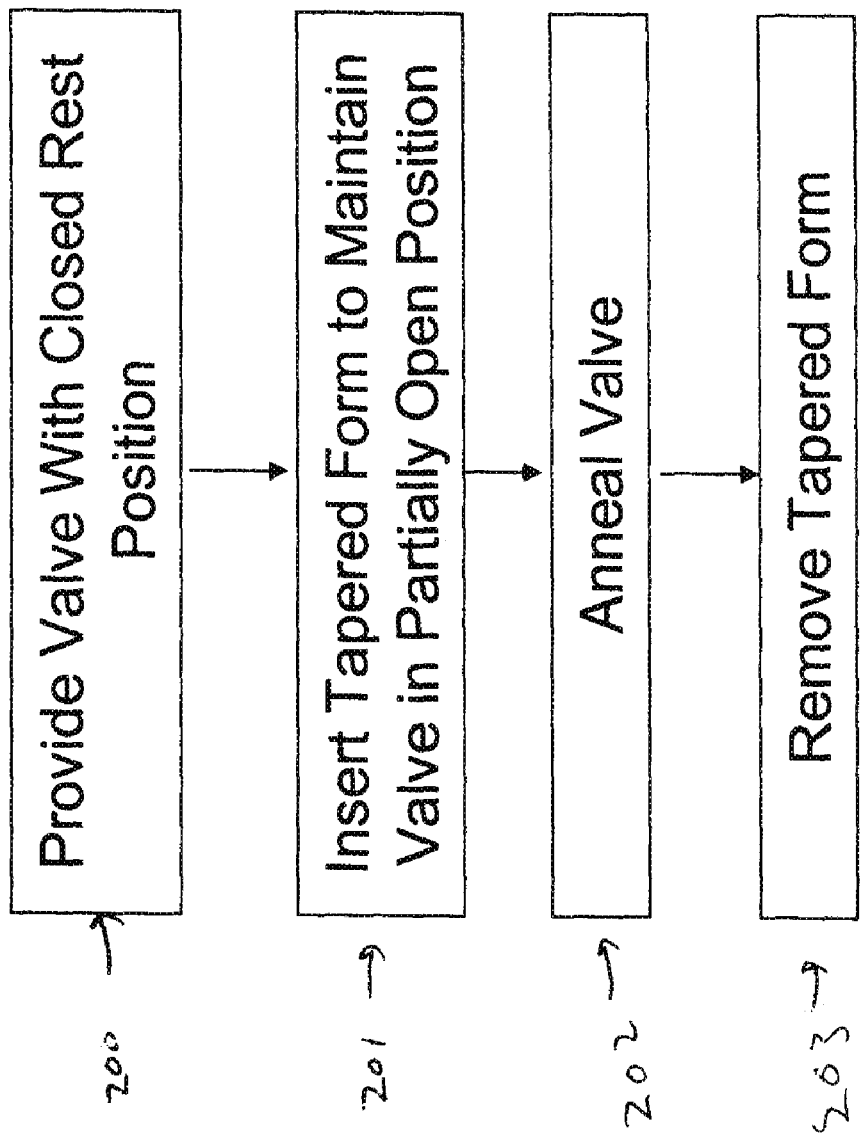
FIG. 4 is s flow chart illustrating the steps of a method of making a polymeric heart valve having partially open rest.
Figure 5A:
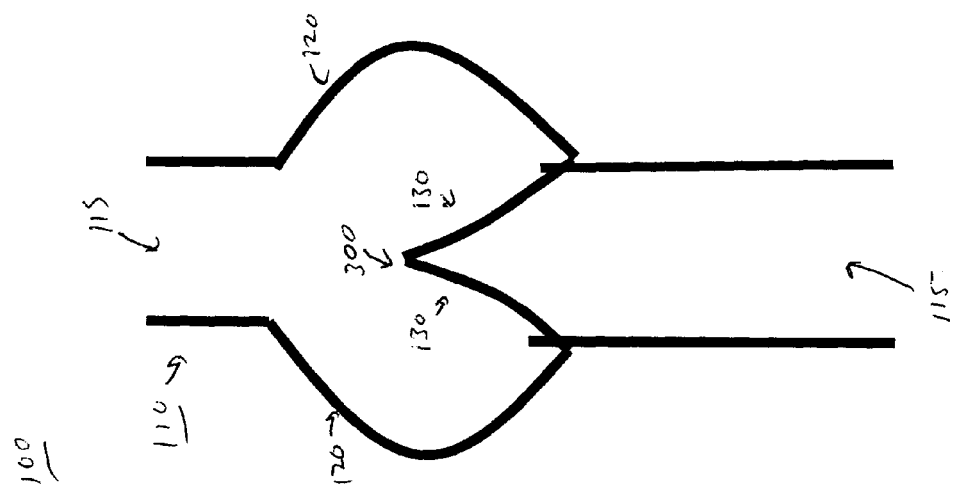
FIGS. 5A-5C are schematic diagrams illustrating a method of making a polymeric heart valve having partially open rest.
Figure 5B:
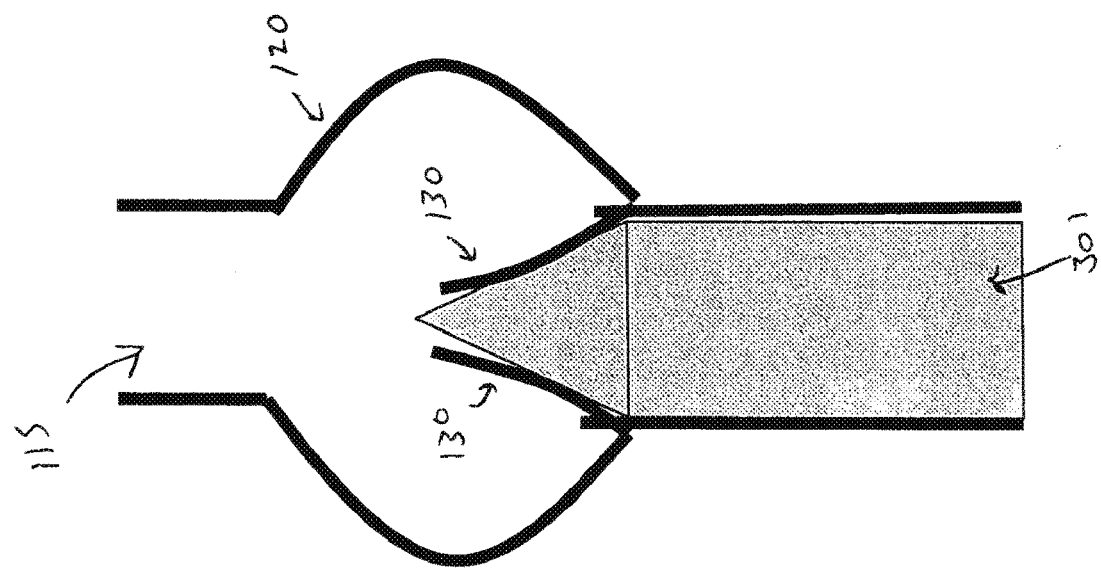

FIG. 4 shows an exemplary flow diagram for a method of making a valve 100 of the type described herein. In a first step 200, an polymeric valve 100 (e.g. a tri-leaflet valve similar to that shown in FIGS. 1A and 1B) is provided which is substantially closed in its rest position, as illustrated in FIG. 5A. That is, the free edges of adjacent leaflets 130 contact each other, thereby substantially impeding fluid flow through the conduit 115. In some embodiments, the rest position of the valve is completely closed, such that the free edges of adjacent leaflets 130 contact each other along their entire lengths and meet at a point 300 (e.g. a triple point for a tri-leaflet valve) to seal off conduit 115.

The polymeric valve formed in the closed position may be constructed using any technique known in the art. For example, some embodiments employ one or more of the fabrication techniques as described in U.S. Pat. No. 4,888,009 issued Dec. 19, 1908, the entire contents of which is incorporated herein by reference. In some such embodiments. a flexible polymeric material is dissolved, e.g. in a volatile solvent, to form a homogeneous syrupy polymer solution (e.g. Angioflex Valve Pouring Solution which can be obtained from Abiomed of Danvers, Mass.). It should be understood that any polymeric substance can be used as the pouring solution.

A highly-polished conduit mandrel, having a portion of diameter slightly greater than that of the inside of the desired conduit 115 (e.g. the downstream conduit including sinus lobes 120 as shown in FIG. 1A) and a wider portion beginning along a contour following the peaks and valleys of a stent, is repeatedly dipped in the polymer solution with interspersed drying periods, to form an extended conduit, e.g. of about 0.3 mm thickness. This conduit assembly is stripped from the mandrel.

A highly-polished leaflet mandrel, matching the contour of the upstream side of the closed leaflets, is inserted into the conduit 115 and carefully aligned. Polymer solution is then poured into the conduit. For example, Angioflex valve pouring solution may be poured into the conduit along one sinus lobe curvature, gradually tilting the conduit/mandrel assembly back from a 45 degree angle to the vertical position and filling the conduit to approximately ⅛" from the top. The pouring solution may then be emptied from the conduit via an adjacent sinus lobe. The assembly is rotated slowly while the solution dries, forming thin leaflets of flexible polymeric material integrally joined to the inside of the conduit. This process is repeated until the leaflets are a desired thickness, e.g. about 0.4 mm thick.

In some embodiments, the rotation process may be performed at varying orientations for different coats. For example, in one embodiments, the rotation is performed with the conduit oriented vertically while the first three coats are applied, and the angle of rotation changed, e.g. to an angle greater than 5 degrees, such as 9 degrees for the remaining pours (e.g. six additional pours). In some embodiments, the valve may be placed on an automated device which controls rotation during the curing process to obtain a desired thickness profile.

After drying, the conduit-leaflet assembly is stripped from the leaflet mandrel. If additional drying is required, the conduit-leaflet assembly may be heated in an oven, e.g. 40° C. until dry, e.g., for 24 hours or more.

The ends of the conduit may be cut to a desired length. For example, in one embodiments, the outflow end of the valve 100 may be trimmed about 32 mm from the bottom of the sinus.

In some embodiments, at least one suture ring (not shown) is coupled to the body above or below the sinus lobes and leaflets to provide a place for sutures to be applied when the valve is implanted. The leaflets 130 may be trimmed, e.g. using a hot wire to very accurately remove material, to have a desired shape and thickness profile (e.g. as described in detailed above).

Figure 5C:
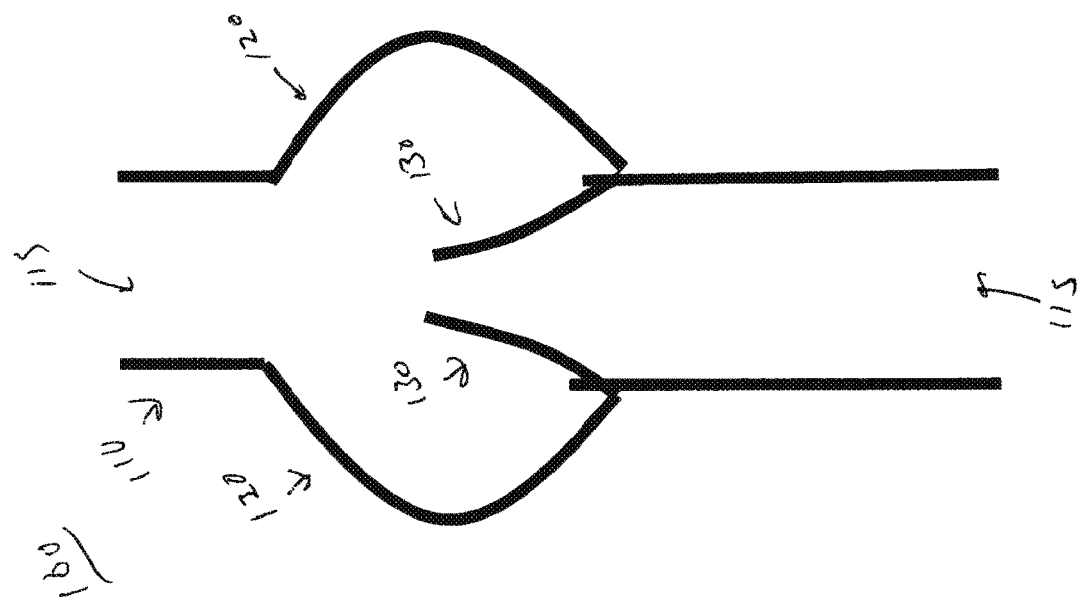

In step 201, as illustrated in FIG. 5C, a tapered form 301 is inserted into the conduit 115 the valve 100 to maintain the leaflets 130 in a partially open position. Tapered form 301 may have a tapered portion having any suitable shape including a conical and pyramidal shape. The tapered portion may come to a point, be rounded, or be truncated. The tapered portion may have any slope, e.g. greater than 10 degrees, 20 degrees, 25 degrees, 45 degrees or more, e.g., about 25 degrees.

In step 202, the valve 100 is heated, e.g. in an oven, to anneal or otherwise cause the valve assembly to be fixed in the partially open rest position. Valve 100 may be heated to any suitable temperature, for example, a temperature greater than 100° C., 125° C., 130° C., or more. The heating may be sustained for any suitable time, e.g. an hour or more. The heating may be followed by a cooling period, for example sufficient for the valve to return to room temperature, e.g., several hours or more.

In step 203, the tapered form 203 is removed. Due to the annealing process, the leaflets 130 remain in a partially open position at rest. Accordingly, the resulting device corresponds to the completed valve 100, e.g., as shown in FIGS. 1A and 1B.

Note that while one exemplary method of forming the valve in the open position is described, others may be used. In some embodiments, the valve is molded in the open position (e.g. using pour molding techniques). In some such cases, the molded valve may contain connecting material between the leaflets which may be used to separate the leaflets. The connecting material may then be cut, e.g., using a laser cutting, hot wire cutting, or mechanical cutting technique to separate the leaflets. Laser cutting in particular is advantageous in that it may provide extremely precise cuts, allowing for a smooth, straight leaflet edge.

Figure 6A:
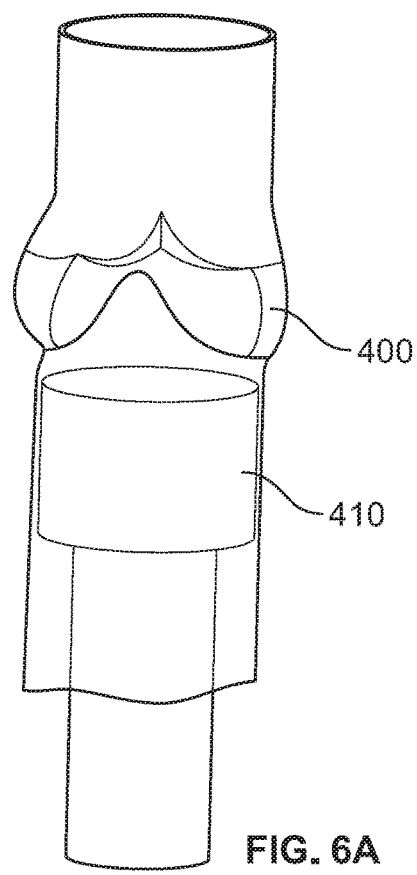
FIGS. 6A-6G are photographs showing an embodiment of a method for forming the leaflets of a polymeric heart valve in a partially open rest position.
Figure 6B:
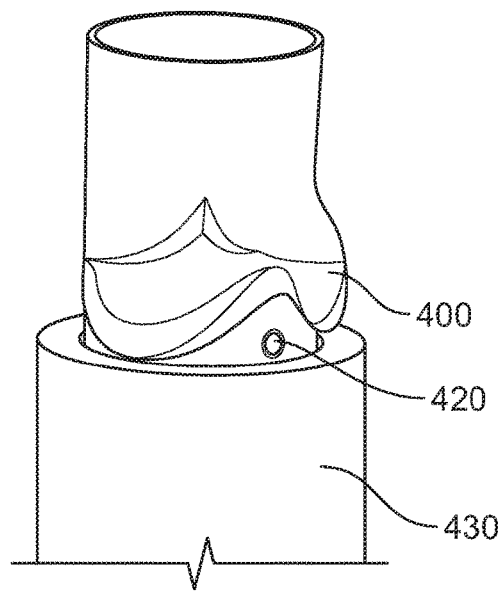
Figure 6C:
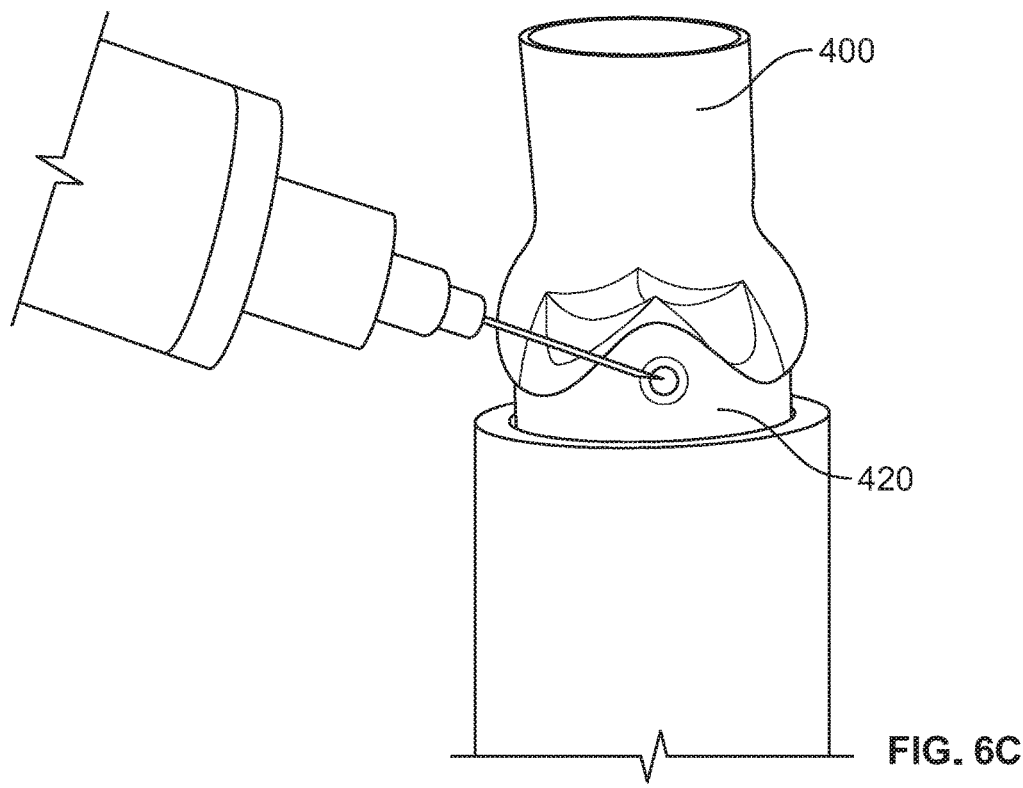

FIGS. 6A-6G show photographs illustrating an embodiment of a method for casting the leaflets of a polymeric heart valve in a partially open position at rest. First, the valve 400 is slid onto mandrel 410. Next, an inflow valve stent 420 is inserted into a stent holder 430. The valve 400 and mandrel 410 are then inserted into the stent holder 430 until the stent 420 cradles the valve conduit as shown in FIG. 6B. Following this, the leaflets should be symmetrically aligned in a substantially closed position. In one embodiment, the leaflets can be observed and aligned using a microscope. Next, once aligned, the stent 420 is tacked in place, e.g. using a UV cured adhesive (FIG. 6C).

Figure 6D:
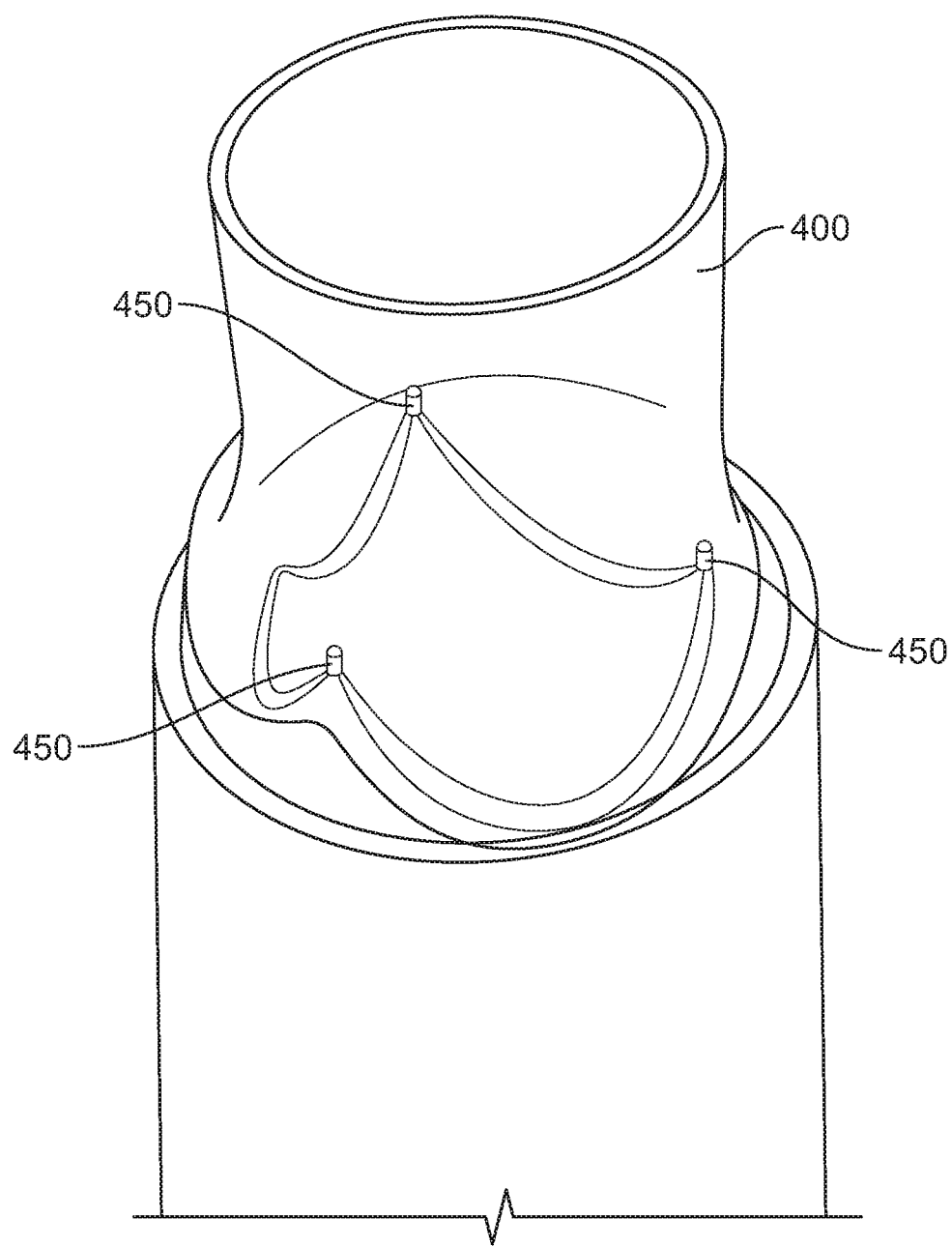
Figure 6E:
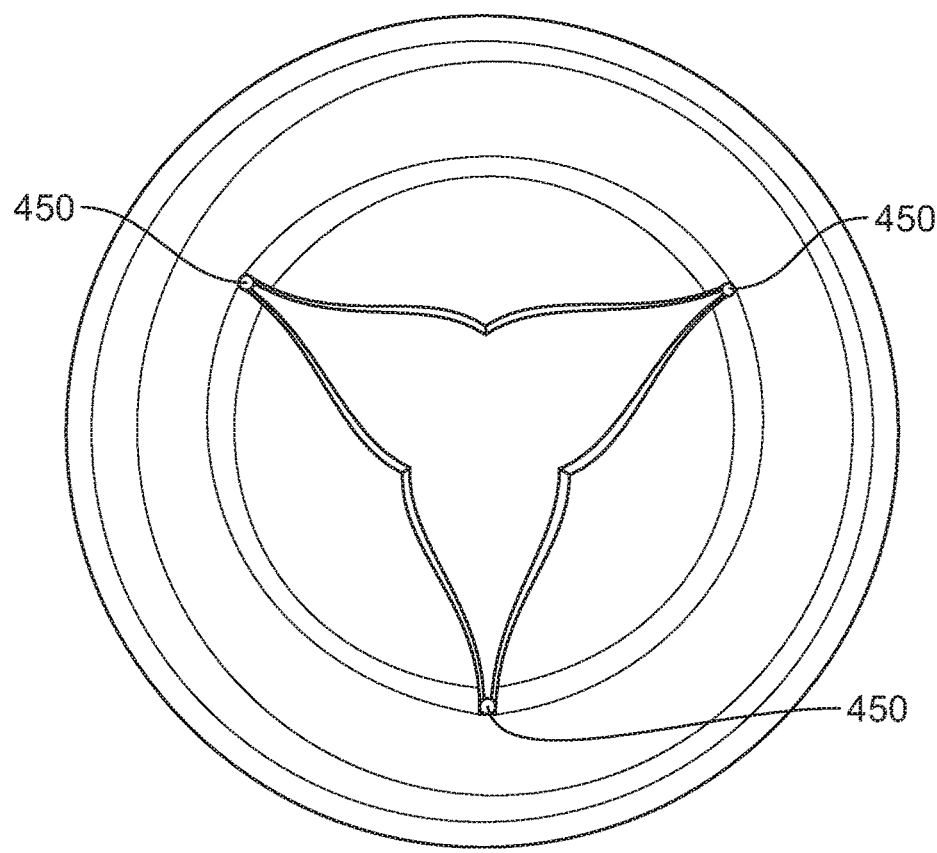

As shown in FIG. 6D, a valve forming cone 440 is placed into the valve assembly 400 so that a pin 450 is against the commissure wall on all 3 commissures. The valve leaflets are now partially open and that the tip of the cone is centered between the tips of the leaflet (FIG. 4E).

The assembly is placed in an oven, and the valve assembly annealed such that the leaflets will remain in the partially open position once the forming cone 440 is removed. In one embodiment, the oven is set at a temperature greater than 100° C., e.g. in the range 125° C.±2 for a suitable time, e.g. 60 minutes or more.

Figure 6F:
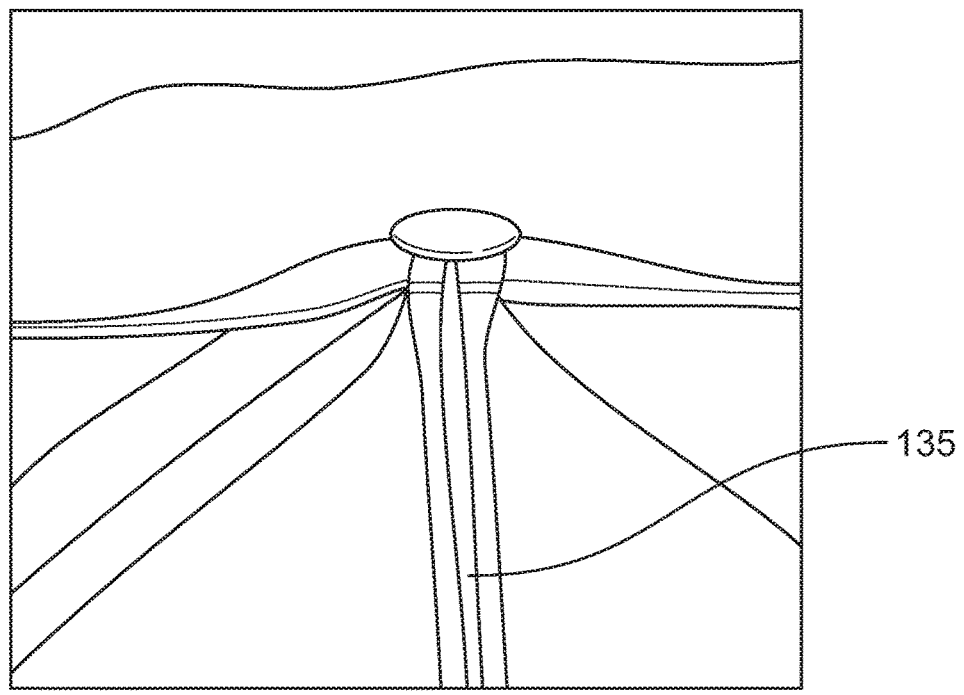
Figure 6G:
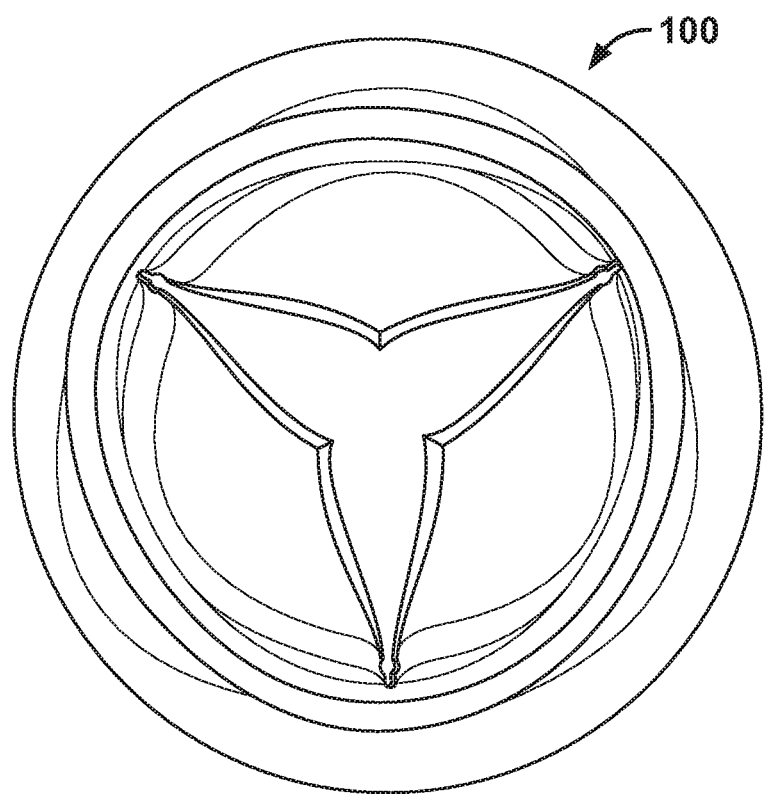

The assembly is removed from the oven and allowed to cool (e.g., for 2 hours or more). The forming cone 440 and pins 450 are removed from the valve 400. The valve may be inspected to verify the commissures are opened properly (FIG. 6F). Similarly, the leaflets may be inspected to verify proper opening (FIG. 6G). It should be understood that in various embodiments the leaflets may not appear in the particular configuration shown, but should in general have a partially opened geometry which maintains the impression left by the cone 440.

It should be understood that other methods of casting the leaflets of a polymeric heart valve in a partially open position at rest can be employed.

The embodiments disclosed herein are to be considered in all respects as illustrative, and not restrictive of the invention. The technology described herein is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A polymeric heart valve, comprising:
   a valve body having a central axis and comprising a conduit extending along the central axis from an inflow end to an outflow end; and
   at least three flexible leaflets extending from the body into the conduit, each of the leaflets defining an attachment curve with the body, a free edge, and a central region between the attachment curve and the free edge;
   wherein respective pairs of leaflets each define;
      a commissure located proximal the body, and
      a gap between the respective pairs, the gap extending from the commissure towards the central axis and having a width;
   wherein each of the at least three leaflets is thicker near the free edge than the central region; and
   wherein the at least three leaflets are configured to define:
      a partially open position where the at least three leaflets maintain a tapered conical form at rest, wherein, in the partially open position, the width of the gap between the respective pairs of leaflets continuously increases from the commissure towards the central axis, a fully open position deflecting away from the central axis during forward blood flow along a direction from the inflow end to the outflow end, and a closed position deflecting toward the central axis during reverse blood flow along a direction from the outflow end to the inflow end.

2. The polymeric heart valve of claim 1, further comprising, for each leaflet, a respective sinus lobe in the conduit extending along the valve body and located distal the respective leaflet from the inflow end.

3. The polymeric heart valve of claim 1, wherein the at least three leaflets open symmetrically in response to forward blood flow.

4. The polymeric heart valve of claim 1, wherein, in the open position, the blood flow velocity through each commissure is substantially the same as that blood flow velocity through the other commissures.

5. The polymeric heart valve of claim 1, wherein each leaflet comprises a pair of free edges coming to a tip near the central axis of the body.

6. The polymeric heart valve of claim 5, wherein each leaflet is characterized by at least a four point thickness profile, wherein: the first point in the profile is substantially located at the tip of the leaflet; the second point and the fourth point in the leaflet are substantially located at respective commissures; the third is substantially located proximal the body substantially midway along the attachment curve between the second and third points.

7. The polymeric heart valve of claim 6, wherein the first point has a thickness ranging between about 0.25 mm and about 0.5 mm.

8. The polymeric heart valve of claim 6 wherein the second point and the fourth point, each has a thickness ranging between about 0.3 mm and about 0.7 mm.

9. The polymeric heart valve of claim 6 wherein the third point has a thickness ranging between about 0.2 mm and about 0.4 mm.

10. The polymeric heart valve of claim 6, wherein the first point has a thickness about equal to or less than two thirds of the thickness of the second and fourth points.

11. The polymeric heart valve of claim 6, wherein the first point has a thickness about equal to or less than one half of the thickness of the second and fourth points.

12. The polymeric heart valve of claim 6, wherein the third point has a thickness about equal to or less than two thirds of the thickness of the second and fourth points.

13. The polymeric heart valve of claim 1, wherein the at rest opening of adjacent leaflets closest to their respective commissure ranges between 0.1 mm and 0.6.

14. The polymeric heart valve of claim 13, wherein the at rest opening of adjacent leaflets closest to their respective commissure is 0.25 mm.

15. The polymeric heart valve of claim 2, wherein the body, sinus lobes, and leaflets are made from a biocompatible polymer.

16. The polymeric heart valve of claim 15, wherein the biocompatible polymer is selected from a group consisting of silicone and/or polyurethane.

17. The polymeric heart valve of claim 16, wherein the body, sinus lobes, and leaflets are integrally constructed.

18. The polymeric heart valve of claim 1, further comprising at least one sewing ring coupled to the body above or below the sinuses and leaflets to provide a place for sutures to be applied when the valve is implanted.

19. A polymeric heart valve prepared by a process comprising the steps of:

forming a polymeric valve comprising:
a valve body having a central axis and comprising a conduit extending along the central axis from an inflow end to an outflow end; and
at least three flexible leaflets extending from the body into the conduit, each of the leaflets defining an attachment curve with the body, a free edge, and a central region between the attachment curve and the free edge;
wherein respective pairs of leaflets each define:
a commissure located proximal the body, and
a gap between the respective pairs, the gap extending from the commissure towards the central axis, and having a width,
wherein each of the at least three leaflets is thicker near the free edge than the central region, and
wherein the leaflets are in a substantially closed at rest position, wherein, in the substantially closed at rest position, the width of the gap between the respective pairs of leaflets continuously increases from the commissure towards the central axis;
inserting a tapered form into the conduit to maintain the at least three leaflets in a partially open position;
heating the polymeric valve to fix the rest position of the at least three leaflets in the partially open position; and
after the heating, removing the form.

* * * * *